United States Patent
Gueller

(10) Patent No.: US 12,138,861 B2
(45) Date of Patent: Nov. 12, 2024

(54) METHOD AND DEVICE FOR THE PRODUCTION OF A THREE-DIMENSIONAL OBJECT

(71) Applicant: Chemspeed Research AG, Liestal (CH)

(72) Inventor: Rolf Gueller, Herznach (CH)

(73) Assignee: Chemspeed Research AG, Liestal (CH)

( * ) Notice: Subject to any disclaimer, the term of this patent is extended or adjusted under 35 U.S.C. 154(b) by 559 days.

(21) Appl. No.: 17/299,338

(22) PCT Filed: Dec. 6, 2019

(86) PCT No.: PCT/EP2019/084052
§ 371 (c)(1),
(2) Date: Jun. 3, 2021

(87) PCT Pub. No.: WO2020/115308
PCT Pub. Date: Jun. 11, 2020

(65) Prior Publication Data
US 2022/0055304 A1  Feb. 24, 2022

(30) Foreign Application Priority Data
Dec. 7, 2018 (CH) ...................... 01516/18

(51) Int. Cl.
*B29C 64/343* (2017.01)
*B29C 64/188* (2017.01)
(Continued)

(52) U.S. Cl.
CPC .......... *B29C 64/343* (2017.08); *B29C 64/188* (2017.08); *B33Y 10/00* (2014.12);
(Continued)

(58) Field of Classification Search
CPC ... B29C 64/209; B29C 64/343; B29C 64/188; B41J 3/4073; B33Y 10/00; B33Y 30/00; B33Y 40/00
See application file for complete search history.

(56) References Cited

U.S. PATENT DOCUMENTS

| 10,760,945 B2 | 9/2020 | Gueller et al. |
| 10,987,666 B2 | 4/2021 | Gueller et al. |

(Continued)

FOREIGN PATENT DOCUMENTS

| CN | 105722663 A | 6/2016 |
| CN | 205460048 U | 8/2016 |

(Continued)

OTHER PUBLICATIONS

"Andrew, the Pipetting Robot Inside Out", https://www.youtube.com/watch?v=952yeU13NQA, Jan. 29, 2015, 1 page.

*Primary Examiner* — Jamel M Nelson
(74) *Attorney, Agent, or Firm* — The Webb Law Firm

(57) ABSTRACT

In a method for the production and/or treatment of a three-dimensional object with a printing material which is dispensed at a target position in the form of discrete three-dimensional printing material elements, a metering device is moved to at least one reservoir in which a supply of printing material is kept and, by means of the metering device, printing material is picked up from that at least one reservoir. The metering device is transported to a target position defined in all three spatial dimensions and, at that target position, a metered quantity of printing material is applied to a substrate or to a three-dimensional object arranged thereon or being constructed thereon, in order to create a printing material element. The creation of a printing material element is repeated until the three-dimensional object has been fully constructed and/or treated. The use of a metering device for picking up, transporting and applying printing material (Continued)

makes it possible for virtually any desired printing materials to be processed and, accordingly, for objects to be produced and/or treated with virtually any desired printing materials.

19 Claims, 11 Drawing Sheets

(51) Int. Cl.
*B33Y 10/00* (2015.01)
*B33Y 30/00* (2015.01)
*B33Y 40/00* (2020.01)
*B41J 3/407* (2006.01)

(52) U.S. Cl.
CPC ............... *B33Y 30/00* (2014.12); *B33Y 40/00* (2014.12); *B41J 3/4073* (2013.01)

(56) References Cited

U.S. PATENT DOCUMENTS

| | | |
|---|---|---|
| 2004/0231593 A1 | 11/2004 | Edwards et al. |
| 2006/0156978 A1 | 7/2006 | Lipson et al. |
| 2006/0160250 A1 | 7/2006 | Bonassar et al. |
| 2006/0211080 A1 | 9/2006 | Frost, III et al. |
| 2007/0179656 A1* | 8/2007 | Eshed .................... B33Y 70/00 700/119 |
| 2012/0116568 A1* | 5/2012 | Murphy ............... B41J 2/04505 414/754 |
| 2015/0105891 A1* | 4/2015 | Golway ................ G06F 30/20 700/98 |
| 2017/0259482 A1* | 9/2017 | Contractor ............ B33Y 30/00 |
| 2017/0322068 A1* | 11/2017 | Gueller ................. B01L 3/0227 |
| 2018/0065186 A1* | 3/2018 | Cullinan ............ H01L 23/4985 |

FOREIGN PATENT DOCUMENTS

| | | | |
|---|---|---|---|
| CN | 108603756 A | 9/2018 | |
| JP | H911337 A | 1/1997 | |
| JP | 2005319618 A | 11/2005 | |
| JP | 2016540664 A | 12/2016 | |
| JP | 2017222163 A | 12/2017 | |
| KR | 1020110060276 A | 6/2011 | |
| NL | 2017088 A | 1/2018 | |
| WO | WO-2015054577 A1 * | 4/2015 | ............ B25J 9/1679 |
| WO | 2015073301 A1 | 5/2015 | |
| WO | 2016074105 A1 | 5/2016 | |
| WO | 2017139332 A1 | 8/2017 | |
| WO | 2017152293 A1 | 9/2017 | |

* cited by examiner

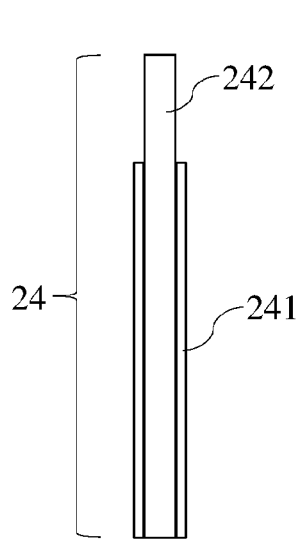 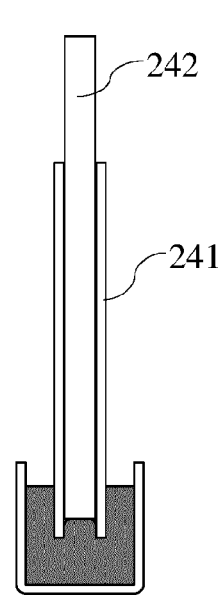 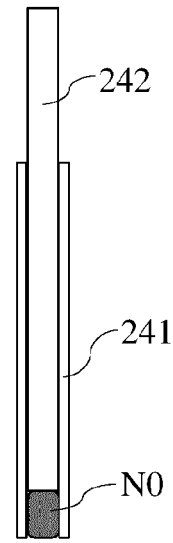
Fig. 8 　　　Fig. 9 　　　Fig. 10
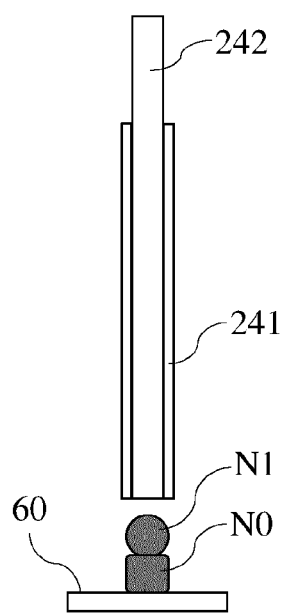 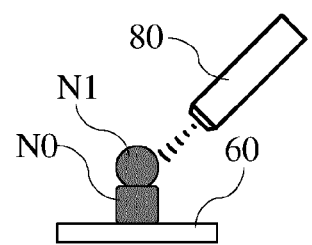 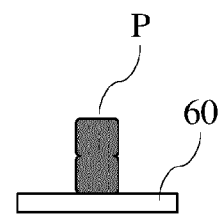
Fig. 11 　　　Fig. 12 　　　Fig. 13

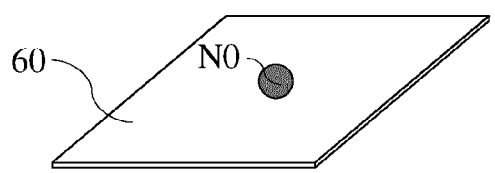
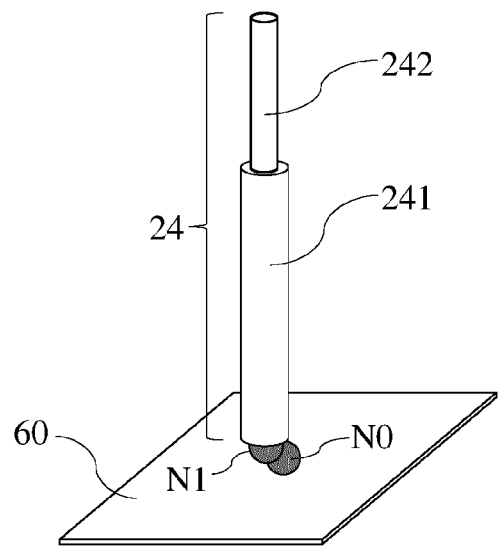
Fig. 14          Fig. 15
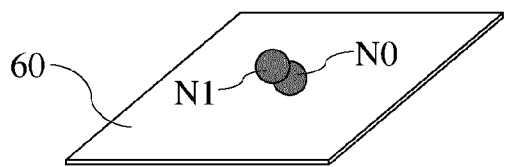
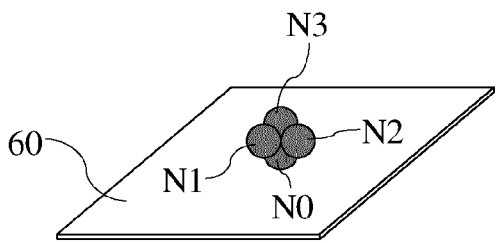
Fig. 16          Fig. 17
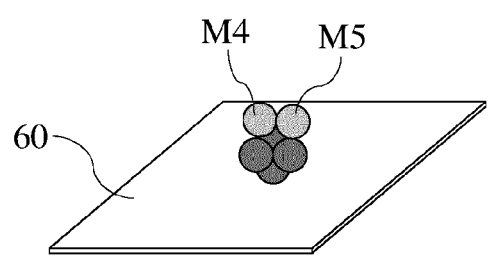
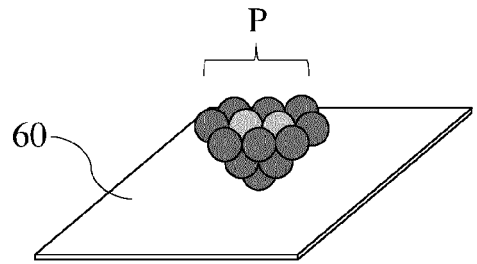
Fig. 18          Fig. 19

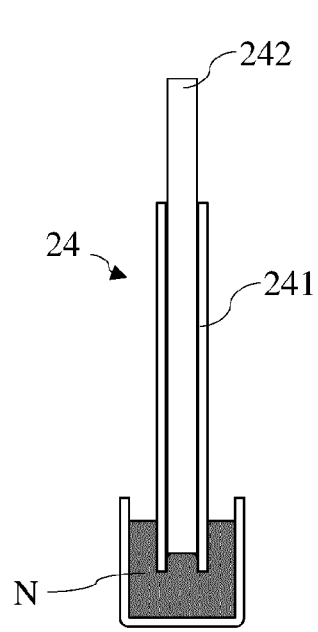
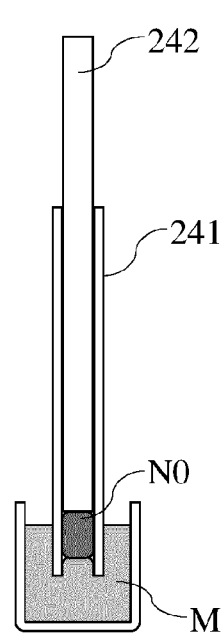
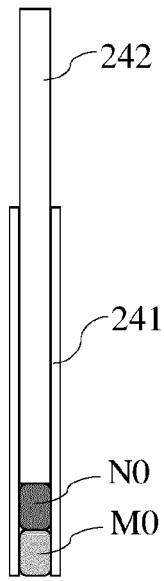
Fig. 23          Fig. 24          Fig. 25
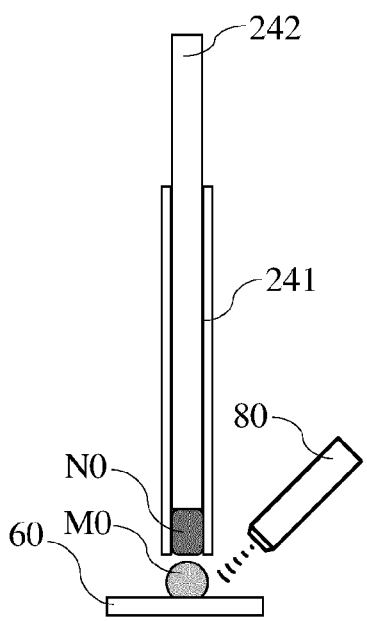
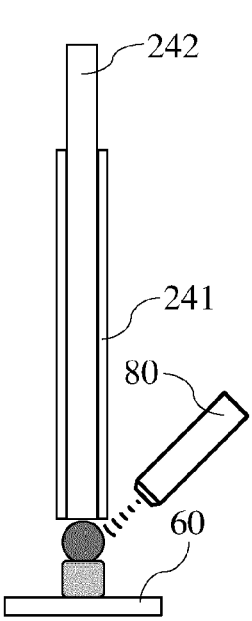
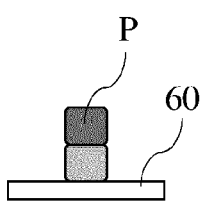
Fig. 26          Fig. 27          Fig. 28

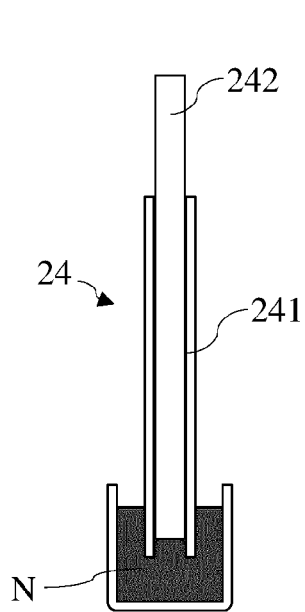
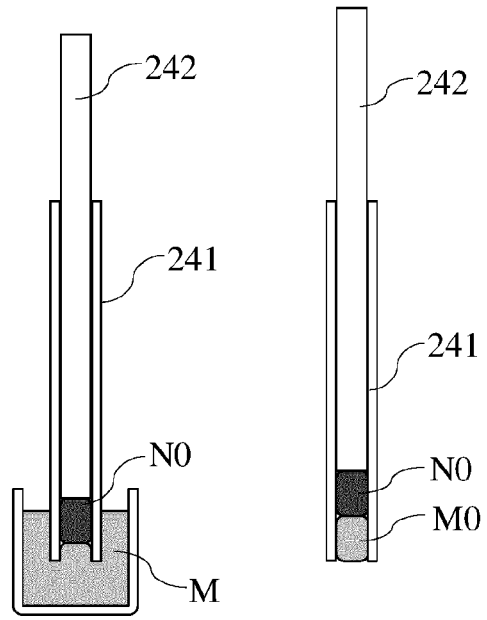
Fig. 29　　Fig. 30　　Fig. 31
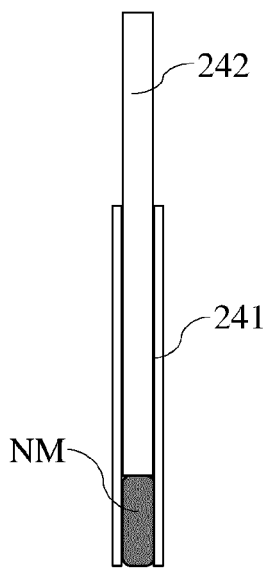
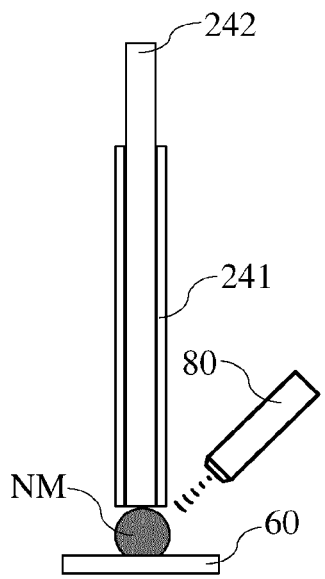
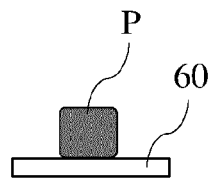
Fig. 32　　Fig. 33　　Fig. 34

METHOD AND DEVICE FOR THE PRODUCTION OF A THREE-DIMENSIONAL OBJECT

CROSS-REFERENCE TO RELATED APPLICATIONS

This application is the United States national phase of International Application No. PCT/EP2019/084052 filed Dec. 6, 2019, and claims priority to Swiss Patent Application No. 01516/18 filed Dec. 7, 2018, the disclosures of which are hereby incorporated by reference in their entirety.

BACKGROUND OF THE INVENTION

Field of the Invention

The present invention relates to a method and a device for the production and/or treatment of a three-dimensional object with a printing material which is dispensed at a target position in the form of discrete three-dimensional printing material elements.

Description of Related Art

The additive manufacturing of three-dimensional objects, commonly referred to as three-dimensional printing or 3D printing, is a rapidly developing manufacturing technology with an increasingly large number of possible applications which include both private applications (for example in the fields of art, model-making, jewellery, fashion, . . . ) and industrial applications (for example fast prototyping, and also the production of standard parts ranging through to the production of food products) in most diverse industrial sectors, in science and research ranging through to medicine and biotechnology (for example manufacturing of prostheses matched to individual patients or even replacement organs from cell cultures). Three-dimensional printing devices are generally referred to as 3D printers.

A typical 3D printer is described, for example, in the document NL 2 017 088 A. That 3D printer comprises a print head, which can be moved by means of a robot arm to any desired target positions inside a working space in order to deposit printing material therein. The printing material is supplied to the print head from a feed unit which is arranged on the robot arm (and accordingly moved therewith). Alternatively, the feed unit can also be arranged in a static position on or close to the base plate of the device, in which case it would then be connected to the print head via corresponding lines.

A device for the production of primarily two-dimensional microstructures on a substrate is disclosed in the document US 2004/0231593 A1. The device contains as its main component an application head which is configured for dispensing metered droplets and which works piezo-electrically in accordance with the inkjet principle. The application head can be moved under computer control in two dimensions to any desired target location of the substrate where it deposits printing material droplet by droplet. The printing material is supplied to the application head either from a reservoir mounted on the application head and/or via a supply line leading to the application head. The device can also have multiple or exchangeable application heads which can also be supplied with different printing materials. Furthermore, that document mentions, although only very generally, that droplets of printing material can also be deposited one on top of the other, with the result that three-dimensional (micro)structures would be generated. 3D printing in the narrower sense, that is to say the generation of macroscopic three-dimensional objects, is not mentioned in that document.

Current 3D printers usually work with a material from which a three-dimensional object is constructed by means of one of several well-established methods (for example fused deposition modelling (FDM/FFF), stereolithography (SLA), digital light processing (DLP), selective laser sintering (SLS), selective (metal) laser melting (SLM) or jetting methods (multi-jet fusion, HSS)).

Increasingly, use is also being made of 3D printers that are able to use a plurality of materials (multiple 3D printing), supplies of which are kept on the printer in question, for example in the form of a plurality of cartridges already prefilled with the different materials or in the form of different selectable reels containing printing materials in wire form (usually plastics, but also metal wires) and which are used as required. Such 3D printers already allow a greater degree of flexibility in respect of the material composition of the end product, that is to say the object to be printed, but in this case too the range of printing materials that can be used is usually limited by the printing method available and is often restricted, for example, merely to the use of different colours of the same type of printing material or to a plurality of readily differentiated materials (for example having different degrees of hardness once the printing materials have cured).

Either way, however, it is not possible, for example, for new or newly developed materials to be used ad hoc, because as a rule it would first be necessary to produce a printable formulation (in the case of liquid application) or a wire-form material. This renders an ad hoc decision impractical, however, and accordingly, for example, even in research and development at least involves an enormous amount of additional expenditure and preparation work and is complex to automate.

In the field of research and development, however, for example in the development of new materials suitable for 3D printing, it is for that reason also a disadvantage that a supply of the printing materials needs to be kept in prefilled containers and metering cartridges or in some other pre-prepared form, because newly developed materials can often be synthesised and/or formulated only in very small amounts, because the material cannot be formulated in the desired form at all (for example because it is in the form of a powder having poor solubility), because a wire serving as printing material would first have to be made from a new type of alloy, or simply because the (manual) filling of suitable metering containers is very laborious and inefficient when it is borne in mind that a material sample is used only once or a small number of times for experiments.

A similar range of problems arises in biotechnology, for example in the production of artificial organs from biomaterials or from cultured cells. In this case too, the printing material must first be produced in sufficient amounts and filled into a suitable metering device (for example a syringe-like cartridge) before it can be used in the 3D printer. In addition, living cells cannot be applied in the frozen state, thus necessitating the use of a cellular suspension.

Furthermore, a scientist working in the field of research and development will often wish to know, for each applied printing material element, how much is being applied and, particularly in the case of new materials which behave differently during metering, will wish to decide shortly before the application of the printing material element to the object being printed whether or not he will apply that printing material element. In that case it is advantageous to be able to decide whether a sufficient quantity of material is being applied, and it should be possible to decide whether or not, for example, too small or too large a material sample is actually to be applied.

SUMMARY OF THE INVENTION

The objective of the present invention is now to provide a method and a corresponding device for the production of a three-dimensional object which avoid the described disadvantages of the known 3D printers and provide additional options especially in terms of selection of materials, range of materials and the combination between different materials and types of material.

Preferably the invention should make it possible, for example, for a researcher to be able simply to test substances present in simple glass containers. Furthermore, in preferred embodiments, for each printing material element to be applied he should be able to decide shortly before application, by using, for example, a pre-programmed decision function (for example "add/apply if error rate is <0.1 mg, otherwise discard and try again"), whether or not the printing material element is applied. In addition, it should preferably be possible also to mix together and then apply extremely small quantities of two or more materials (for example a difficultly soluble powder in a liquid, etc.).

The problem underlying the invention is solved by the method according to the invention defined in independent patent claim 1 and by the device defined in independent patent claim 19. Especially advantageous developments and embodiments of the method according to the invention and of the device according to the invention are the subject matter of the respective dependent patent claims.

In respect of the method, the core of the invention lies in the following: for the production and/or treatment of a three-dimensional object with a printing material which is dispensed at a target position in the form of discrete three-dimensional printing material elements, a metering device is moved to at least one reservoir in which a supply of printing material is kept. Printing material is picked up from that at least one reservoir by means of the metering device. The metering device is moved to a target position defined in all three spatial dimensions and, at that target position, a metered quantity of printing material is applied by means of the metering device to a substrate or to a three-dimensional object arranged thereon or being constructed thereon, in order to create a printing material element. The creation of a printing material element is repeated until the three-dimensional object has been fully constructed and/or treated.

The use of a metering device for picking up, transporting and applying printing material makes it possible for virtually any desired printing materials to be processed and, accordingly, for objects to be produced and/or treated with virtually any desired printing materials.

Advantageously, a supply of two or more different printing materials is kept and different printing materials are selected and picked up in order to construct and/or treat the three-dimensional object with different printing materials.

In an advantageous embodiment, the printing material or printing materials used are liquids, solids dissolved or suspended in liquids, cellular suspensions or biomaterials.

In a further advantageous embodiment, the printing material or printing materials used are penetrable or amorphous solids or frozen substances. Penetrable or amorphous solids are to be understood as being, for example, wax-like substances, or substances such as, for example, chocolate.

In a further advantageous embodiment, the printing material or printing materials used are pulverulent or granular solids.

In an advantageous embodiment, by means of the metering device in each case a quantity of printing material is picked up that corresponds quantitatively to a printing material element. The quantity of printing material to be dispensed or applied by the metering device thus corresponds exactly to the quantity of printing material picked up.

In an advantageous embodiment, the quantity of printing material picked up in each case is weighed gravimetrically before application to the substrate or to the three-dimensional object being constructed thereon and, based on the result of weighing and preset criteria, a decision is made as to whether the quantity picked up is supplemented or discarded and a new quantity picked up. This allows the quality of the three-dimensional object being constructed or treated to be improved.

In an advantageous embodiment, the quantity of printing material applied, in the form of a printing material element, by the metering device in the target position to the substrate or to the three-dimensional object arranged thereon or being constructed thereon is hardened and/or fused to the substrate or to the three-dimensional object arranged or already partly constructed thereon by application of directed radiation or heat or by some other hardening or polymerising method. The individual printing material elements are thereby locally fixed in position.

The metering device advantageously comprises an exchangeable metering tool, the metering tool being discarded and replaced by a fresh metering tool prior to a change of the printing material to be picked up. Contamination problems are thereby avoided.

Alternatively, the metering tool is cleaned prior to a change of the printing material to be picked up.

In an advantageous embodiment, the construction and/or treatment of the three-dimensional object is partly effected by means of an additional printing system which is itself likewise configured for the production and/or treatment of a three-dimensional object, in which case printing material elements are applied to the substrate or to the three-dimensional object arranged thereon or being constructed thereon both by means of the metering device and by means of the additional printing system. As a result, for example, basic structures of the three-dimensional object can be constructed by means of the additional printing system and further structures can be added to those basic structures by means of the metering device, it being possible for those further structures to consist, for example, of printing materials which cannot be processed by means of the additional printing system.

In an advantageous embodiment, at least one printing material is configured so that the printing material element applied to the substrate or to the three-dimensional object arranged thereon or being constructed thereon has a material-removing action, so that material is removed from the three-dimensional object. A three-dimensional object can thus also be broken down, that is to say subtractively treated, point by point. The method according to the invention therefore not only can be used for additive manufacturing but, if required, can also be used subtractively.

In an expedient embodiment, the material-removing action occurs only after activation of the printing material element, especially after activation by means of heat or radiation. In that way, for example, temporary supporting structures can be removed once they are no longer needed.

In order that the applied printing material element has a material-removing action, the at least one printing material can be, for example, in the form of an acid or solvent.

In a further advantageous embodiment, at least one printing material is configured so that the printing material element applied to the substrate or to the three-dimensional object arranged thereon or being constructed thereon modifies the physical or chemical properties of the three-dimensional object point by point. This can be utilised, for example, for point-by-point modification of the conductivity of those parts of the three-dimensional object which consist, for example, of silicon, especially for doping of the silicon.

In a further advantageous embodiment, by means of the metering device different printing materials are picked up one after the other from at least two reservoirs and transported to a target position defined in all three spatial dimensions and, at that position, the different printing materials are applied one after the other to the substrate or to the three-dimensional object arranged thereon or being constructed thereon. The construction or treatment of the three-dimensional object can thus be accelerated.

Alternatively, by means of the metering device different printing materials are picked up one after the other from at least two reservoirs, transported to a target position defined in all three spatial dimensions and, at that position, applied to the substrate or to the three-dimensional object arranged thereon or being constructed thereon, the different printing materials being mixed with one another in the metering device prior to application. This can make it possible to accelerate the construction of the object, especially in the case of two-component systems.

In a further advantageous embodiment, the metering device has at least two metering channels by means of which printing material or printing materials is/are picked up, one after the other or simultaneously, from one or more reservoirs and then transported to at least one target position defined in all three spatial dimensions and, at that position, applied to the substrate or to the three-dimensional object arranged thereon or being constructed thereon. The construction or treatment of the three-dimensional object can thus be accelerated.

In respect of the device, the core of the invention lies in the following: a device for the production and/or treatment of a three-dimensional object with a printing material comprises an apparatus for dispensing printing material in the form of discrete three-dimensional printing material elements at a target position. It comprises a metering device which is configured to pick up printing material from at least one reservoir in which a supply of printing material is kept. It further comprises a transport device which is configured to move the metering device to the at least one reservoir and to transport the metering device to a target position defined in all three spatial dimensions. The metering device is further configured to apply the printing material that it has picked up, in a metered amount, to a substrate or to a three-dimensional object arranged thereon or being constructed thereon.

The metering device for picking up, transporting and applying printing material allows the processing of virtually any desired printing materials and, accordingly, the production and/or treatment of objects made from virtually any desired printing materials.

Advantageously the metering device has at least one metering tool provided in a holder, which metering tool is configured to be installed in a metering head of the metering device and removed again therefrom, the transport device being configured to move the metering head to the metering tool provided in the holder and to install the metering tool in the metering head. Furthermore, the transport device is configured to move the metering device together with the installed metering tool over the reservoir and to dip the metering tool into the supply of printing material kept therein, whereby a defined quantity of the printing material can be picked up by the metering tool. The use of metering tools that are installable in the metering head means that it is always possible to use an optimum metering tool for each printing material and in accordance with the size of the printing material element to be dispensed.

Preferably the transport device comprises a handling robot controlled by a control computer. The handling robot is advantageously configured so that it achieves a spatial positioning accuracy of at least 100-200 µm, preferably down to 1-2 µm.

In advantageous embodiments, the device comprises a plurality of reservoirs for the same or different printing materials, the reservoirs being formed by individual containers or by a plate, which preferably has a plurality of wells, especially made of glass or plastics. Even without wells, the plate can act as one or more containers for printing materials heaped thereon.

In an advantageous embodiment, the device comprises a plurality of metering tools provided in the holder, and the metering tools are in the form of tubes or capillaries of different sizes into which printing material can be introduced and dispensed again therefrom. The provision of a plurality of different metering tools makes it possible to select the most suitable tool in each case.

Advantageously the tubes have a plunger movable therein, it being possible for a defined quantity of printing material to be picked up by drawing in liquid printing material by retraction of the plunger and to be dispensed from the tube again by forward movement of the plunger. Preferably the plunger is longer than the tube and projects from the tube at the upper end thereof.

Advantageously the tubes have a plunger movable therein, it being possible for a defined quantity of printing material to be picked up by insertion of a tube into solid or amorphous printing material or powder or granules and to be dispensed from the tube again by forward movement of the plunger. Preferably the plunger is longer than the tube and projects from the tube at the upper end thereof, the plunger being retracted in the tube prior to insertion and thus allowing a defined quantity of printing material to be picked up when the tube is inserted into solid or amorphous printing material or powder or granules, which quantity can then be ejected from the tube again by forward movement of the plunger. The plunger can be loosely movable in the tube and need not slide tightly therein, that is to say need not seal the tube.

Tubes as metering tools have proved satisfactory in other applications and are best suited for the device according to the invention. Alternatively, the metering tools can also be in the form of disposable syringes. The latter are also very suitable for the device according to the invention.

In other advantageous embodiments, instead of tubes it is also possible to use solid bodies having a cylindrical, rod-like, spherical or other shape, which are especially dipped into liquid or pulverulent printing material, so that a small droplet or a small quantity of powder adheres to the metering tool and can then be set in place. In that case the metering tools are preferably in the form of differently sized rods, to one end of which printing material adheres when the rod is dipped into printing material. This is particularly useful when especially small quantities are being metered and allows very fine resolution and very small structures.

In an advantageous embodiment, the device can also be equipped with a heater or radiation source for heating the metering tool in the state in which it is installed in the metering head. As a result, the quantity of printing material present in the metering tool can, for example, be kept in the molten state while it is being transported to the target position or application point.

In an advantageous embodiment, the device expediently has at least one radiation source for high-precision action on the printing material quantity applied to the substrate or to the three-dimensional object arranged thereon or being constructed thereon. Accordingly, the applied printing material elements can be melted, cured or cross-linked and locally fixed in position.

Advantageously the at least one radiation source is arranged on the metering head. As a result, the laborious alignment of the radiation source with the target position is unnecessary.

The metering tool is expediently configured so that the radiation emitted by the at least one radiation source is conductible through the metering tool to the applied printing material quantity.

The at least one radiation source is advantageously configured for the melting or hardening of printing material.

Advantageously the device comprises two or more reservoirs for different printing materials and is configured for selecting printing material from different reservoirs and for picking up that printing material in the metering tool, it being possible for the three-dimensional object to be constructed from two or more different printing materials.

In an advantageous embodiment, the device comprises at least one additional independent printing system which is itself likewise configured for the production and/or treatment of a three-dimensional object. The device is preferably configured for constructing and/or treating the three-dimensional object partly by means of the metering device and partly by means of the additional printing system. As a result, for example, substructures of the object can be constructed and/or treated by means of the additional printing system and further structures can be added to those substructures by means of the metering device, it being possible for those further structures to consist, for example, of printing materials that cannot be processed by means of the additional printing system. The universal applicability of the device is thereby increased.

In a further advantageous arrangement, the device can also be used to remove constituents of the three-dimensional object, for example by point-by-point application of suitable solvents or acids, for which purpose a supply of such a solvent or such an acid is kept in at least one reservoir.

In a further advantageous embodiment, the metering device has at least two metering channels by means of which printing material or printing materials can be picked up, one after the other or simultaneously, from one or more reservoirs and then transported to at least one target position defined in all three spatial dimensions and, at that position, applied to the substrate or to the three-dimensional object arranged thereon or being constructed thereon. The construction or treatment of the three-dimensional object can thus be accelerated.

BRIEF DESCRIPTION OF THE DRAWINGS

The invention is described in greater detail below with reference to exemplary embodiments shown in the drawings, wherein:

FIG. 8-13—show a diagrammatic sectional view of a metering tool during various working steps of the construction of a three-dimensional printed object;

FIG. 14-19—show a diagrammatic perspective detail view of the construction of a three-dimensional printed object during various working steps of the printing process;

FIG. 23-28—show a diagrammatic sectional view of a metering tool during various working steps of the construction of a three-dimensional printed object with two different unmixed printing materials;

FIG. 29-34—show a diagrammatic sectional view of a metering tool during various working steps of the construction of a three-dimensional printed object with two different printing materials which are mixed together;

DESCRIPTION OF THE INVENTION

The following observations apply in respect of the description which follows: where, for the purpose of clarity of the drawings, reference signs are included in a Figure but are not mentioned in the directly associated part of the description, reference should be made to the explanation of those reference signs in the preceding or subsequent parts of the description. Conversely, to avoid overcomplication of the drawings, reference signs that are less relevant for immediate understanding are not included in all Figures. In that case, reference should be made to the other Figures.

The units of quantity of the printing material applied to the respective support (the substrate or the three-dimensional object arranged or being constructed thereon) in each printing step are referred to as printing material elements irrespective of their specific geometric form. In the context of the invention, printing material elements are to be understood both as being points of printing material in the narrower sense and as being linear or planar printing material structures.

Figure 1:
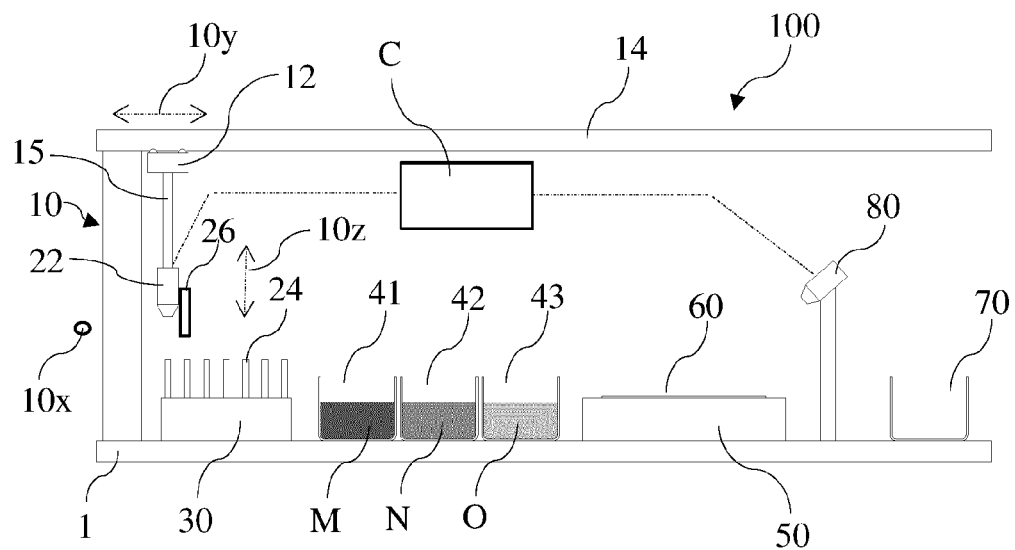
FIG. 1-7—show a diagrammatic view of a first exemplary embodiment of the device according to the invention during various working steps of the printing process.

FIG. 1 shows a first exemplary embodiment of the device according to the invention in the idle state. The device, which is denoted as a whole by reference numeral 100, has been set up on a base plate 1 on which a handling robot 10 is arranged. A metering head 22 is mounted on the handling robot 10. The handling robot 10, which is shown only diagrammatically in the drawing, is configured to move the metering head 22 mounted thereon to any desired spatial coordinate inside the device 100, and accordingly constitutes a transport device for the metering head. The handling robot 10 is movable as a whole back and forth relative to the base plate 1 perpendicularly to the plane of the drawing in the direction of the arrow 10x indicated herein only by a circle (in this connection see also FIG. 20). A carriage 12 is arranged so as to be movable to the left and right along a robot arm 14 extending in the direction of arrow 10y, and a robot arm 15 arranged on the carriage 12, which arm carries the metering head 22, is able to move the metering head 22 up and down in the direction of arrow 10z. The handling robot 10 is controlled by a control computer C. The handling robot 10 can also have further axes (for example for rotation of the robot arm 15) or it can also be, for example, in the form of a linear robot, articulated arm robot, SCARA robot, delta robot etc. What is important is merely that, as already mentioned, the metering head 22 is able to move to any desired spatial coordinate inside the device 100, it being advantageous for the handling robot 10 to allow at least the same spatial resolution and positioning accuracy as in commercial 3D printers, that is to say at least 100-200 μm, advantageously down to 1-2 μm. The handling robot 10 shown in the drawing corresponds to the prior art, as illustrated, for example, by the document WO 2016/074105 A1.

On the base plate 1 there are arranged a holder 30 for metering tools 24, (here, for example, three) reservoirs 41, 42 and 43 for, in this case, different printing materials M, N, O, an analytical balance 50 with a substrate 60 clamped thereon, a waste container 70 for used metering tools 24, and a radiation source 80.

The metering head 22 is configured, with the aid of the handling robot 10, to pick up metering tools 24, deploy them and release them again. The metering head 22, together with a picked-up metering tool 24, forms a metering device 20. The metering device 20 shown in the drawing corresponds to the prior art, as illustrated, for example, by the documents WO 2016/074105 A1 or WO 2017/152293 A1. The metering head 22 can, however, also be realised in some other way, provided it is configured to pick up, deploy and release metering tools. The metering device can also, for example, be formed by a commercial metering device, such as a liquid handler, cartridge dispenser, etc.

The handling robot 10 allows the metering device 20 to move in different spatial axes so that the metering device is able to travel both to printing material reservoirs and to any desired point on the three-dimensional object to be printed.

The holder 30 holds a number of metering tools 24. The metering tools 24 are in the form of tubes or capillaries 241 with a plunger 242 sliding therein (see also FIG. 8-11); they form a cavity, for example by retraction of the plunger 242, so that a quantity of printing material defined by the size of the cavity remains in the metering tool 24. Thus, for example, a liquid can be drawn up. The metering tool 24 so configured is equally suitable for being inserted into solid, waxy, granular or pulverulent solids and for picking up sub-quantities thereof. The exact mode of operation of such metering tools is described, for example, in the document WO 2016/074105 A1.

Alternatively, the metering tools can also be in the form of commercial automatic pipettes having disposable tips or syringes, which function, for example, in accordance with the air displacement principle or the positive displacement principle. Their functioning is familiar to the person skilled in the art and is therefore not described in further detail.

Figure 21:
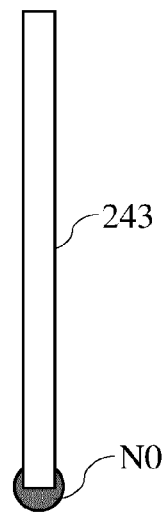
FIG. 21—shows an alternative form of a metering tool.

As a further alternative, the metering tools can also be simply in the form of non-hollow solid bodies without a cavity, for example in the form of thin rods to which a small quantity of substance adheres when they are dipped/inserted into the printing material, which quantity can then be dispensed on the three-dimensional object (for example by the application of a dot of substance, see also FIG. 21). The exact mode of operation of such metering tools is described, for example, in the document WO 2017/152293 A1.

The reservoirs 41, 42 and 43 hold a supply of three or more different printing materials M, N and O. Alternatively, the printing materials can also be provided in other types of vessel, for example in plates having a plurality of wells (for example, what are known as microtitre plates, MTP), in which small quantities of printing material are stored (see also FIG. 20).

In an advantageous embodiment, the supply of printing materials provided in the reservoirs comprises most diverse materials at the same time, for example different liquids, solids (for example waxy, granular or pulverulent), and also frozen liquids ("Cryo-3D printing"), solutions and suspensions, ranging through to whole cell cultures having living cells, which are stored in suitable vessels. This means that for each defined point of the three-dimensional object it is possible exactly to define which of the stored materials can be used, this further allowing the production of objects with a greater range and complexity of materials than possible hitherto. In addition to the use of printing materials from which a three-dimensional object is constructed additively, it is of course also possible to employ materials that remove existing structures/objects point by point, for example by etching away/dissolving away with acids or solvents, respectively.

It is also possible for supplies of only relatively small quantities of printing materials to be kept in the reservoirs 41, 42 and 43. The filling and, if applicable, refilling of those reservoirs can then be effected from corresponding sources either by means of the metering device 20 or by means of a separate metering device. This variant is especially advantageous, for example, if some of the printing materials used are to be produced in a different device (for example a synthesis device or formulation device) physically close to the printing device and are to be used for testing in the printing device. In that case it would be advantageous to use a device having small wells (for example a microtitre plate) as reservoir (see also FIG. 20).

An alternative option is not to keep a supply of the printing materials but to produce them directly on the device by means of suitable tools and methods. This can especially be important if the printing material itself cures rapidly once it has been synthesised or formulated (for example two-component adhesives etc.).

The substrate 60 clamped on the analytical balance 50 serves as base for the three-dimensional object P to be constructed.

The radiation source 80, which, for example, is in the form of a laser or UV radiation source, serves to harden/cross-link or fuse individual printing material elements to one another (for details see below). The radiation source can advantageously be mounted in the printing device and be controllable (by the control computer C) so that it is able specifically to irradiate any desired point in the space above the substrate in order to melt(fuse), to harden or to crosslink the material located at that point. In another advantageous embodiment, the radiation source is mounted directly on the metering head 22 and is oriented so that it is always exactly targeted on the tip of the metering tool 24 installed in the metering head 22, so that a printing material element dispensed at that location can be fused, hardened or crosslinked immediately after it has been dispensed (see also FIG. 20).

The analytical balance 50 serves for gravimetric measurement of the quantity of printing material dispensed by the metering device 20. Alternatively or in addition, the quantity of printing material picked up by the metering device can advantageously also be measured gravimetrically by means of a further analytical balance. One possibility is for the reservoirs to be arranged on an analytical balance so that the quantities of printing material removed therefrom can be determined. An especially suitable arrangement for determining the quantities of printing material picked up by the metering device or by the metering tool thereof is shown diagrammatically in FIG. 22.

Figure 22:
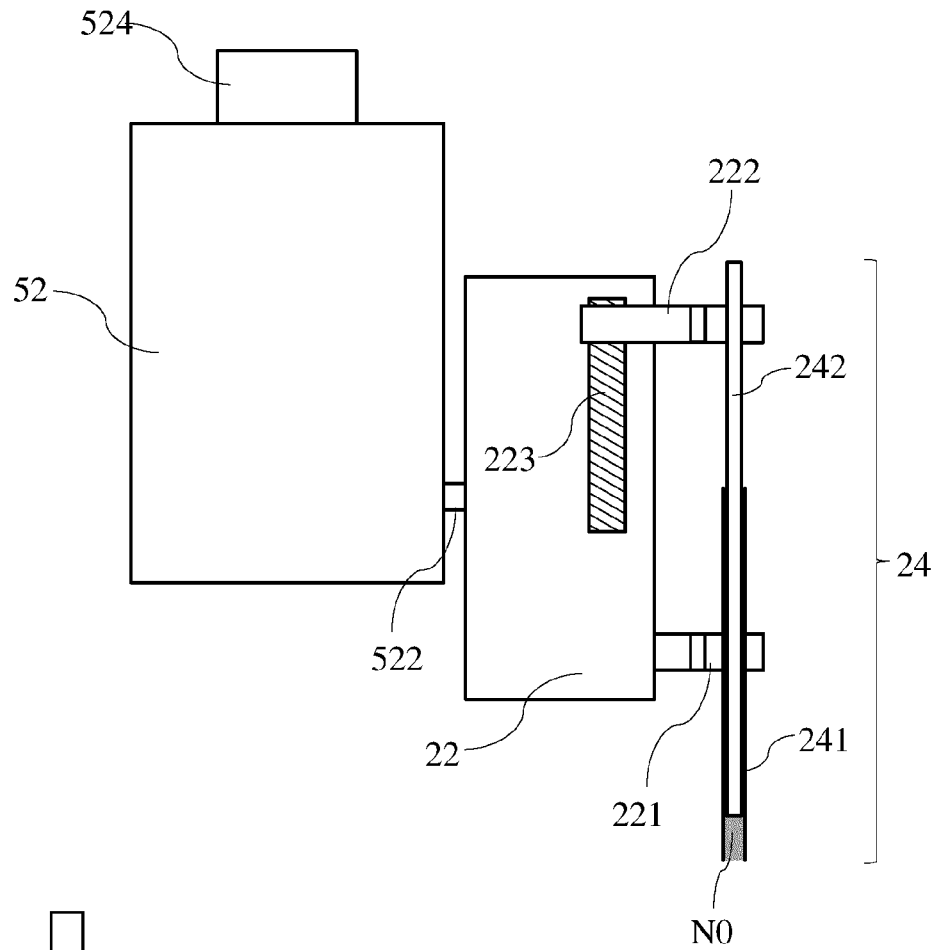
FIG. 22—shows a diagrammatic view of a detail variant of the device.

In that arrangement the metering head 22 is suspended on an analytical balance 52 via a connection piece 522, so that the analytical balance 52 measures the weight of the metering head 22 with all the objects, especially a metering tool 24, attached thereto. The analytical balance 52 is connected via a connection piece 524 to the handling robot 10 (not shown herein). As can also be seen from FIG. 22, the metering head 22 is equipped with two pairs of gripping tongs 221 and 222. The lower gripping tong pair 221 in FIG. 22 is stationary with respect to the metering head 22 and serves for holding/releasing a metering tool 24 or in this case its tube 241. The other gripping tong pair 222 can be moved up and down by means of a drive 223 and serves for holding/releasing the plunger 242 of the metering tool 24 and for moving the latter upwards and downwards. The two pairs of gripping tongs 221 and 222 and the drive 223 are likewise controlled by the control computer C (not shown herein). A more detailed explanation can be found, for example, in the document WO 2016/074105 A1.

By means of the analytical balance 52 the weight of a clamped metering tool 24 with or without picked-up printing material can be measured before and after the printing material has been picked up and also after the printing material has been dispensed. In this way the quantity of printing material element to be applied to the three-dimensional object can be accurately determined. On the basis of the quantity of material measured it is also possible to decide whether the printing material element in question should be applied at all or is to be discarded. If the quantity is too small, the metering tool can, for example, be inserted or dipped into the corresponding reservoir once more in order to pick up additional printing material. If the quantity is too large, the metering tool can be discarded and fresh printing material picked up using a different, possibly smaller metering tool.

Figure 2:
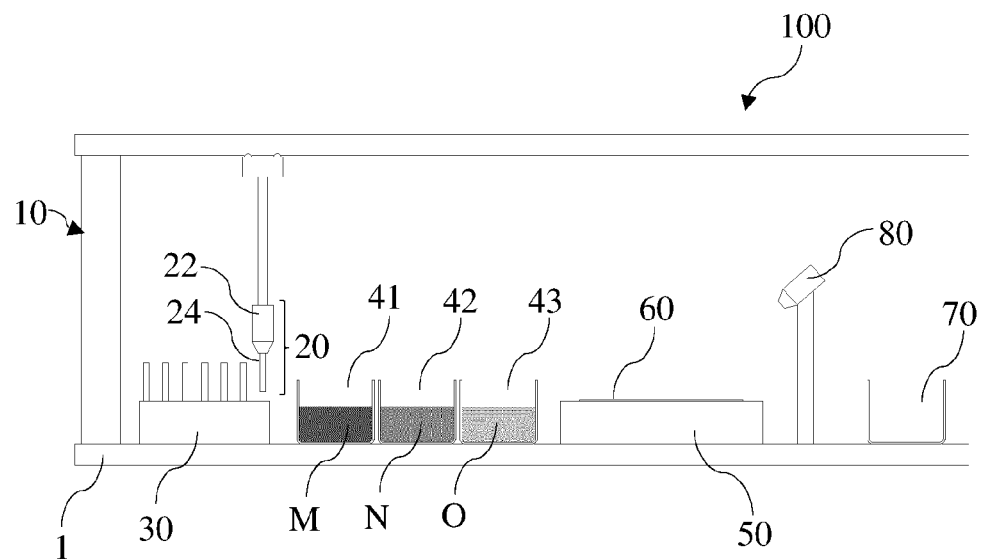
Figure 3:
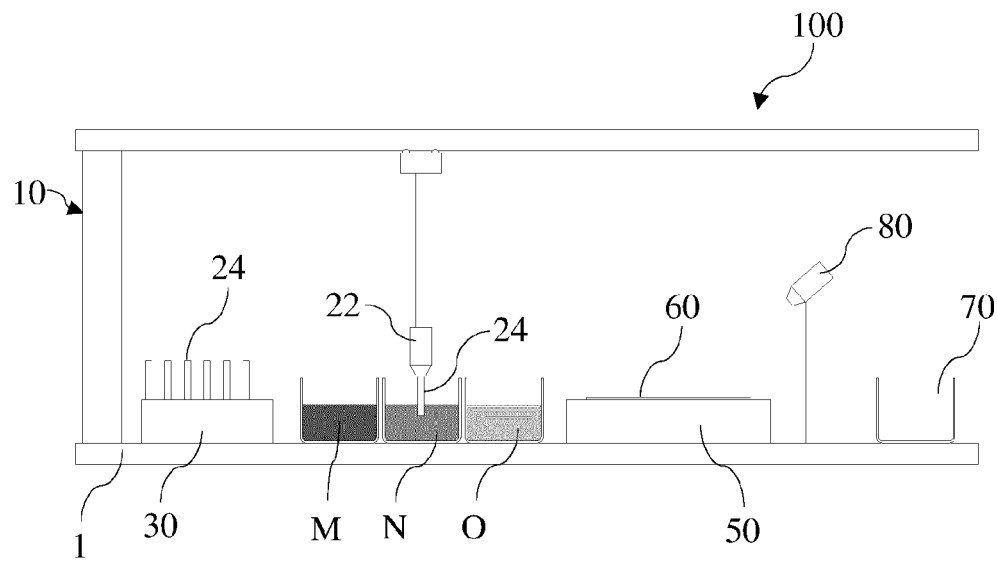

FIG. 2 shows a first working step of the printing device 100 according to the invention. The metering head 22 is moved by the handling robot 10 to the holder 30 where it picks up a metering tool 24 which here consists, for example, of a tube 241 and a plunger 242 displaceably arranged therein. In a next step (FIG. 3), if the printing material N stored in the reservoir 42 is a solid or a highly viscous liquid or suspension, the metering tool 24 is inserted therein or, if the printing material N is a liquid, the metering tool is dipped therein. In the case of a liquid or suspension, the plunger 242 (FIG. 8-11) of the metering tool 24 is then retracted in order to pick up a defined quantity of printing material N (see also FIG. 9) so that the quantity N0 (see FIG. 10) remains in the cavity formed between the plunger 242 and the tube 241. The exact quantity N0 can be controlled by the distance by which the plunger 242 is retracted and by the internal diameter of the tube 241. Tubes having an internal diameter of from 0.1 to 1 mm are usually suitable, depending upon the nature of the printing material to be processed.

Figure 4:
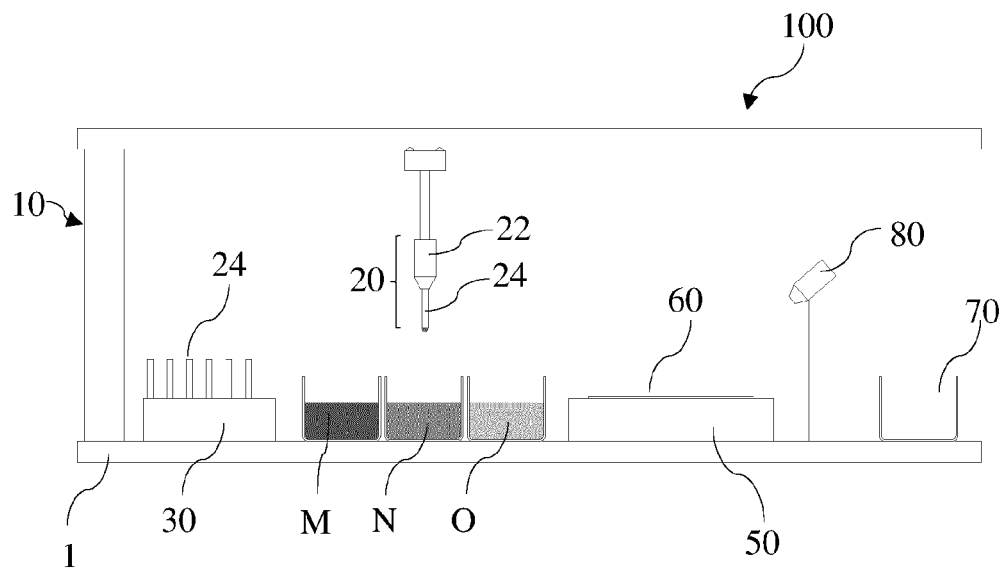
Figure 5:
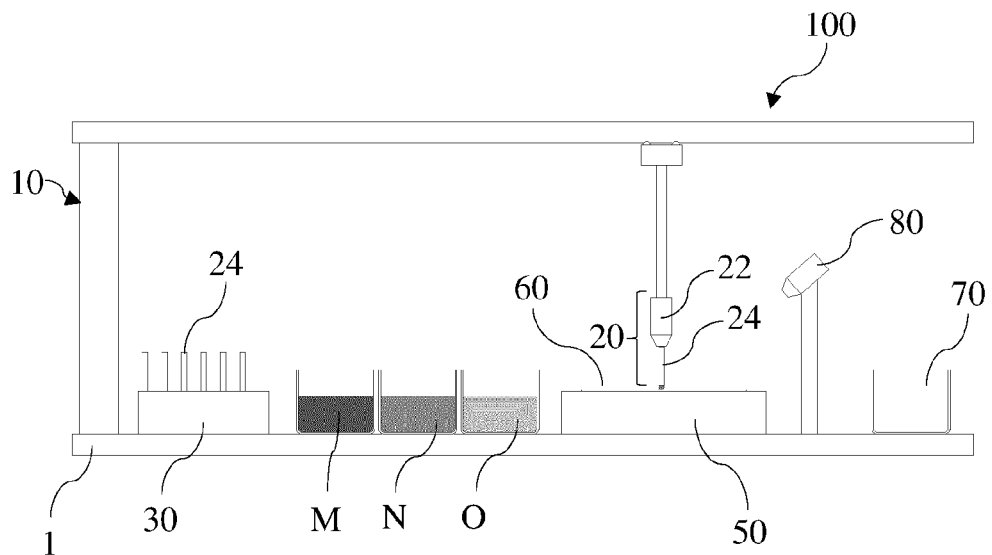
Figure 6:
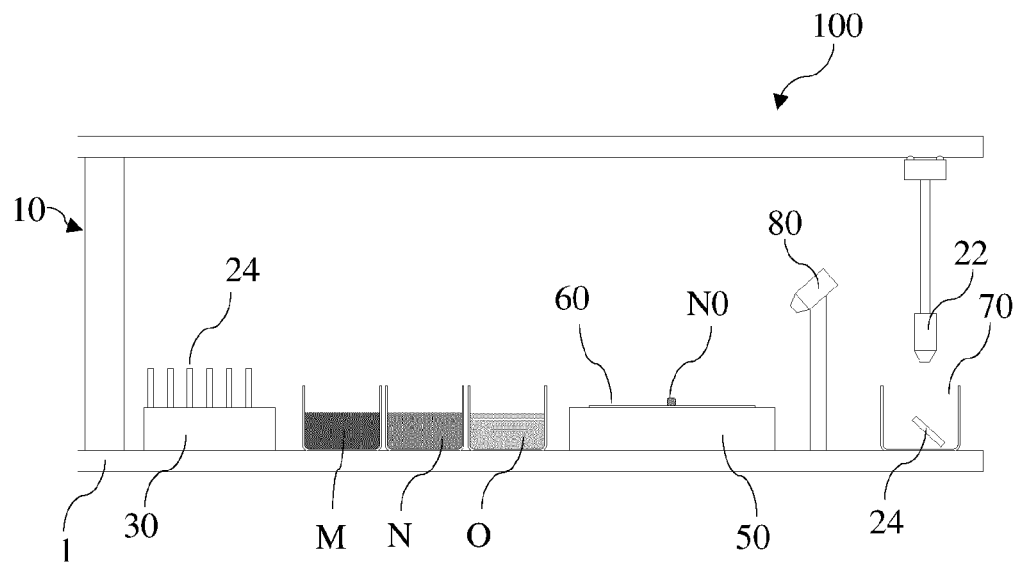

After the printing material quantity N0 has been picked up/drawn up into the metering tool 24, the metering tool is lifted out of the printing material N again (FIG. 4) and then moved to the substrate 60 where the printing material quantity N0 is applied, at a precisely defined location on the substrate S, as first printing material element of the three-dimensional object P to be produced (FIG. 5). For that purpose the material quantity N0 is ejected from the metering tool 24 by downward movement of the plunger 242 inside the metering tool 24 by means of the metering head 22 and applied to the substrate S. Of course, it is also possible for several portions of the same printing material to be picked up simultaneously by a metering tool, which portions can then be set in place one after the other and independently of one another on the three-dimensional object P. The first printing material element N0 is hardened or crosslinked by irradiation or by the action of heat by means of the radiation source 80 (for example a laser suitable for the corresponding printing material) (FIG. 6).

Figure 7:
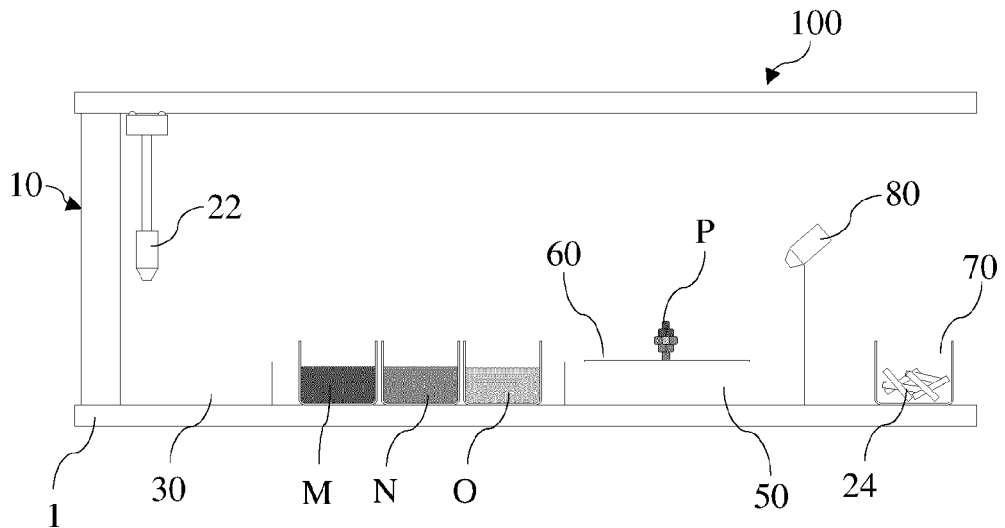

If further printing material elements of the same type are then to be used for constructing the object P, the dipping/picking up/dispensing sequence as described in FIGS. 3-6 is repeated in order to set printing material element on printing material element (see also FIG. 14-17) in order to create a three-dimensional object P. If sufficient printing material has been picked up, if need be a plurality of printing material elements can also be applied one after the other without it being necessary for the metering tool 24 to be dipped intermediately into the reservoir. If, however, a different printing material (in this case, for example, M or O) is to be employed, the used or contaminated metering tool 24 with which the material N was metered is discarded into the waste container 70 (FIG. 6) and the printing operation is continued with a different printing material analogously to the steps described in FIG. 2-5 until finally the end product, consisting of a multiplicity of individual printing material elements that have been fused to one another or hardened, is obtained as a finished three-dimensional object P (FIG. 7). Alternatively, it would also be possible for used soiled metering tools not to be discarded before the next metering steps but simply to be cleaned by means of a suitable washing device inside the device.

FIG. 8-13 show detail steps of the printing method according to the invention. FIG. 8 shows a metering tool 24, in this case in a simple form consisting of a tube 241 made of glass (other materials are also suitable, however, depending upon the printing materials to be used) in which a slightly longer plunger 242 (advantageously likewise made of glass) is slidably mounted. The plunger 242 can be moved up and down relative to the tube 241 by means of the metering head 22 or the handling robot 10.

FIG. 9 shows how the metering tool 24 is dipped into a printing material N—a liquid in the example shown—which is drawn into the tube 241 by retraction of the plunger 242. In the case of a solid (for example powder, granules or an amorphous solid) the plunger would already have been retracted by a defined distance (in order to obtain a cavity of defined size) before insertion into the solid, and the tool would then be inserted into the solid, whereby a portion of the solid would pass into the tube 241 and remain therein.

FIG. 10 shows a metering tool 24 completely filled with a defined quantity N0 of printing material, as is the case, for example, during movement of the metering device 20 from the reservoir 42 to the substrate 60.

FIG. 11 shows how a quantity N1 of printing material transported in the metering tool 24 is moved to its target position (in this case directly on top of a printing material element N0 that has already been previously set in place on the substrate 60 and hardened), precisely positioned, and pushed out of the metering tool 24 and applied to the printing material element N0 by downward movement of the plunger 242.

As shown in FIG. 12, the printing material element N1 just applied is hardened/crosslinked or fused to the printing material element N0 already deposited by the action of heat/radiation/laser beam (depending upon the printing material) generated by means of the radiation source 80, so that a three-dimensional object P is created from the two printing material elements (FIG. 13). Should the production of the three-dimensional object require printing materials having different melting/hardening/crosslinking methods, it will be understood that the printing device according to the invention is also equipped with a plurality of melting/hardening/crosslinking devices respectively suitable for the different printing materials (see also FIG. 20). Depending upon the printing material, it may also be possible entirely to dispense with hardening or melting or crosslinking and corresponding devices, that being the case, for example, with printing materials that cure or solidify without external action (for example self-drying materials, two-component systems, . . . ).

FIG. 21 shows an alternative, rod-shaped metering tool 243 which can simply be dipped into the printing material (in this case N), whereby a quantity N0 of printing material adheres to the tool and can then be set in place on the object P.

Figure 20:
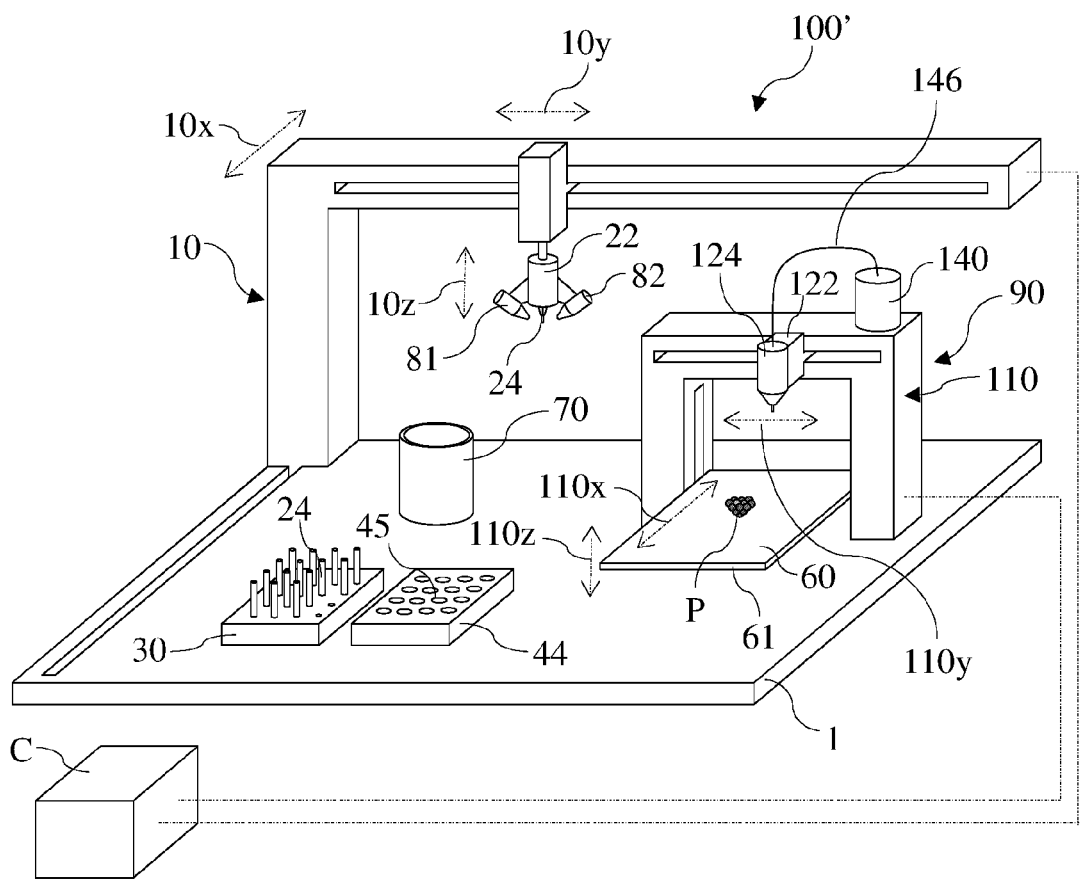
FIG. 20—shows a diagrammatic view of a further exemplary embodiment of the device according to the invention with an integrated additional printing system.

The movements of the metering head 22 by means of the handling robot 10 in the three spatial directions for picking up or discarding a metering tool 24, for dipping the metering tool 24 into a printing material and for removing it therefrom, and for positioning the metering tool at the desired deposition location on the substrate 60 or on the three-dimensional object P being constructed thereon, are controlled by the control computer C as in the exemplary embodiment shown in FIG. 20, as is likewise the drawing-in of printing material into the metering tool 24 and the ejection thereof from the metering tool and the activation of the radiation source 80.

For that purpose, the control computer uses process control information which, for each individual point to be printed (or for each line if the metering tool is being moved in one or more spatial axes during dispensing), comprises the spatial coordinates thereof, the identity of the material and the quantity of material as well as the printing sequence of all individual points of the three-dimensional object.

FIG. 14-19 show the actual printing operation in a very simplified perspective view in order to clarify the construction of a three-dimensional object P from individual printing material elements. FIG. 14 shows a substrate 60 with a first printing material element N0 already applied thereto. FIG. 15 shows how, by means of the metering tool 24, a second printing material element N1 is applied to the printing material element N0 (the melting/hardening operation is not shown in FIG. 14-18 for reasons of clarity) so that, as shown in FIG. 16, a simple object is created from two printing material elements.

FIG. 17 shows the object being constructed, with two further printing material elements N2 and N3 which in this example together form a simple inverted tetrahedron. FIG. 18 then shows how two further printing material elements M4 and M5, but this time made of a different printing material M, have been added to the object. Finally, FIG. 19 shows a further later manufacturing step in which further printing material elements made of material N have already been added to the object P. It can readily be seen how a three-dimensional printed object P consisting of different printing materials can be constructed by means of the printing device 100 according to the invention.

The device according to the invention can also have a heater 26 (shown diagrammatically only in FIG. 1) in order, for example, to keep the quantity of printing material contained in the metering tool 24 in the molten state while it is being transported to the application point.

A second exemplary embodiment of the device according to the invention for the production of a three-dimensional object is shown diagrammatically and in a highly simplified form in FIG. 20. The device 100' again comprises, as already explained above, a handling robot 10 which is able to move a metering head 22 in all three spatial directions (arrows 10x, 10y and 10z) in order thus, by means of the metering head 22, to pick up a metering tool 24 from a holder 30, to pick up printing material from a reservoir (in this case in the form of a plate 44 having a plurality of wells 45 containing different printing materials), to construct the three-dimensional object P and to discard the used metering tool 24 into a waste container 70.

In this exemplary embodiment, a plurality (in this case specifically two) radiation sources 81 and 82 are mounted directly on the metering head 22 and oriented so that they are targeted on the tip of the metering tool 24 installed in the metering head 22. This allows a plurality of different printing materials that make different demands on the radiation source for hardening or melting to be used in the device, without the device as a whole being altered.

A control computer C again controls the handling robot 10 and the (in this case two) radiation sources 81 and 82 and also the metering head 22 in the way already explained in connection with the first exemplary embodiment.

In addition, in this second exemplary embodiment an independent printing system 90 is also integrated into the printing device 100', which printing system is itself likewise configured for the production of a three-dimensional object. The additional printing system 90 can be provided, for example, by a conventional 3D printer.

In the example shown in the drawing, the additional printing system 90 comprises a drive device, denoted as a whole by reference numeral 110, by means of which, on the one hand, a plate-like substrate support 61, to which a substrate 60 is attached, can be moved forwards and backwards (arrow 110x) in its plane and upwards and downwards (arrow 110z) perpendicular to its plane and, on the other hand, a print head 122, on which a metering device 124 is mounted, can be moved to the left and right (arrow 110y) parallel to the plane of the substrate support 61. Overall the metering device 124 can accordingly be moved into any desired spatial position relative to the substrate support 61 or relative to the substrate 60 attached thereto. The metering device 124 is supplied with a printing material, for example a liquid printing material, from a reservoir 140 via a line 146, and the metering device 124 is configured to dispense printing material point by point in order to construct a three-dimensional object P therefrom on the substrate 60. The additional printing system 90 is, as already mentioned, provided by a conventional 3D printer and therefore does not require more detailed explanation. In principle a large number of different 3D printer types and technologies can be used for the additional printing system 90, for example also the 3D printer described in the document NL 2 017 088 A.

The handling robot 10 is likewise able to move the metering device 20, consisting of a metering head 22 and a metering tool 24, attached thereto to any desired spatial position relative to the substrate support 61 or relative to the substrate 60 attached thereto, so that, as already explained above, a three-dimensional object P can also be constructed on the substrate 60 by means of the metering device 20. Accordingly, both the metering device 20 and the metering device 124 of the integrated printing system 90 are then capable of working on the same object P being constructed on the substrate 60. In that case the control computer C assumes the control of the additional printing system 90 as well as the coordination of the processes, in order, on the one hand, to prevent collisions and, on the other hand, to ensure optimum construction of the object.

This second exemplary embodiment of the device according to the invention has the advantage that it is capable of more universal use. Thus, a three-dimensional object can be constructed either by means of the metering device 20 or by means of the integrated printing system 90 or, advantageously, by means of both in combination. For example, the integrated printing system 90 could construct the basic structure of the object being produced, while further structures made of printing materials not processible by the integrated printing system 90 could be added by means of the metering device 20. In order even further to increase the range of possible applications of the device according to the invention, the device can also be equipped with two or more additional printing systems.

FIG. 23-28 show detail steps of an embodiment of the printing method according to the invention for accelerated construction of a three-dimensional object with two different unmixed printing materials N and M. FIG. 23 again shows the metering tool 24 with the tube 241 and with the plunger 242 which can be moved up and down relative to the tube 241 by means of the metering head 22 or the handling robot 10. The metering tool 24 has been dipped into a printing material N, which is drawn into the tube 241 by retraction of the plunger 242.

FIG. 24 shows the metering tool 24 filled with a defined quantity N0 of printing material after being withdrawn from the printing material N and dipped into the printing material M. Printing material M is drawn into the tube 241 by further retraction of the plunger 242.

FIG. 25 shows the metering tool 24 filled with the defined printing material quantity N0 and the defined printing material quantity M0, the two different printing materials not having been mixed together. In this state the metering tool 24 is moved to the substrate 60.

FIGS. 26 and 27 show how the printing material quantity M0 and the printing material quantity N0 are precisely positioned in their target position on the substrate 60 and on the printing material element M0, respectively, and pushed out of the metering tool 24 and applied by downward movement of the plunger 242. The action of the radiation source 80 effects fusing or hardening/crosslinking so that a three-dimensional object P is created from the two printing material elements M0 and N0 (FIG. 28).

FIG. 29-34 show detail steps of an embodiment of the printing method according to the invention for accelerated construction of a three-dimensional object with two different printing materials N and M which are mixed together. FIG. 29 shows in turn the metering tool 24 with the tube 241 and with the plunger 242 which can be moved up and down relative to the tube 241 by means of the metering head 22 or the handling robot 10. The metering tool 24 has been dipped into a printing material N which is drawn into the tube 241 by retraction of the plunger 242.

FIG. 30 shows the metering tool 24 filled with a defined quantity N0 of printing material after being withdrawn from the printing material N and dipped into the printing material M. Printing material M is drawn into the tube 241 by further retraction of the plunger 242.

FIG. 31 shows the metering tool 24 filled with the defined printing material quantity N0 and the defined printing material quantity M0, the two different printing materials not yet having been mixed together. The two printing material quantities N0 and M0 can be mixed with one another in the metering tool 24 or in the tube 241, for example by generating turbulence by upward and downward movement of the plunger 242, so that the mixture NM is formed, see FIG. 32. The metering tool 24 is moved to the substrate 60 before, during or after mixing.

FIG. 33 shows how the mixture NM as printing material element is precisely positioned in its target position on the substrate 60 and pushed out of the metering tool 24 and applied by downward movement of the plunger 242. The action of the radiation source 80 effects fusing or hardening/crosslinking so that a three-dimensional object P is created (FIG. 34).

Figure 35:
FIG. 35-38—show in diagrammatic form the treatment of a three-dimensional object with printing material elements having a material-removing action.

FIG. 35-38 show the treatment of a three-dimensional object P on a substrate 60 with printing material elements having a material-removing action. FIG. 35 shows the as yet untreated three-dimensional object P on the substrate 60.

Figure 36:
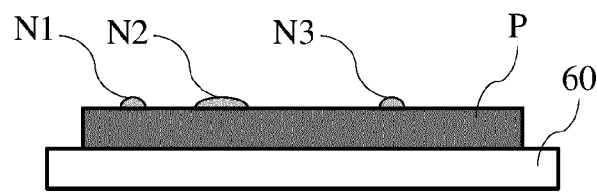
Figure 37:
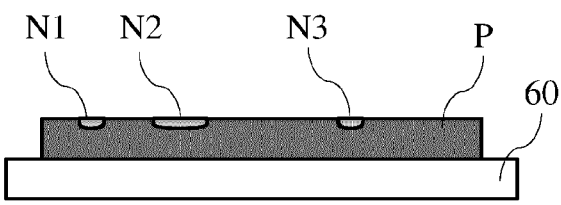

FIG. 36 shows the situation immediately after application of three printing material elements N1, N2 and N3 to the three-dimensional object P. In FIG. 37 the printing material elements N1, N2 and N3 have already eaten into the three-dimensional object P, i.e. have removed the corresponding material from the object P.

Figure 38:
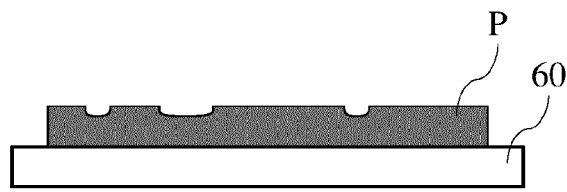

FIG. 38 shows the situation after the printing material elements N1, N2 and N3 have been removed, for example washed out.

Figure 39:
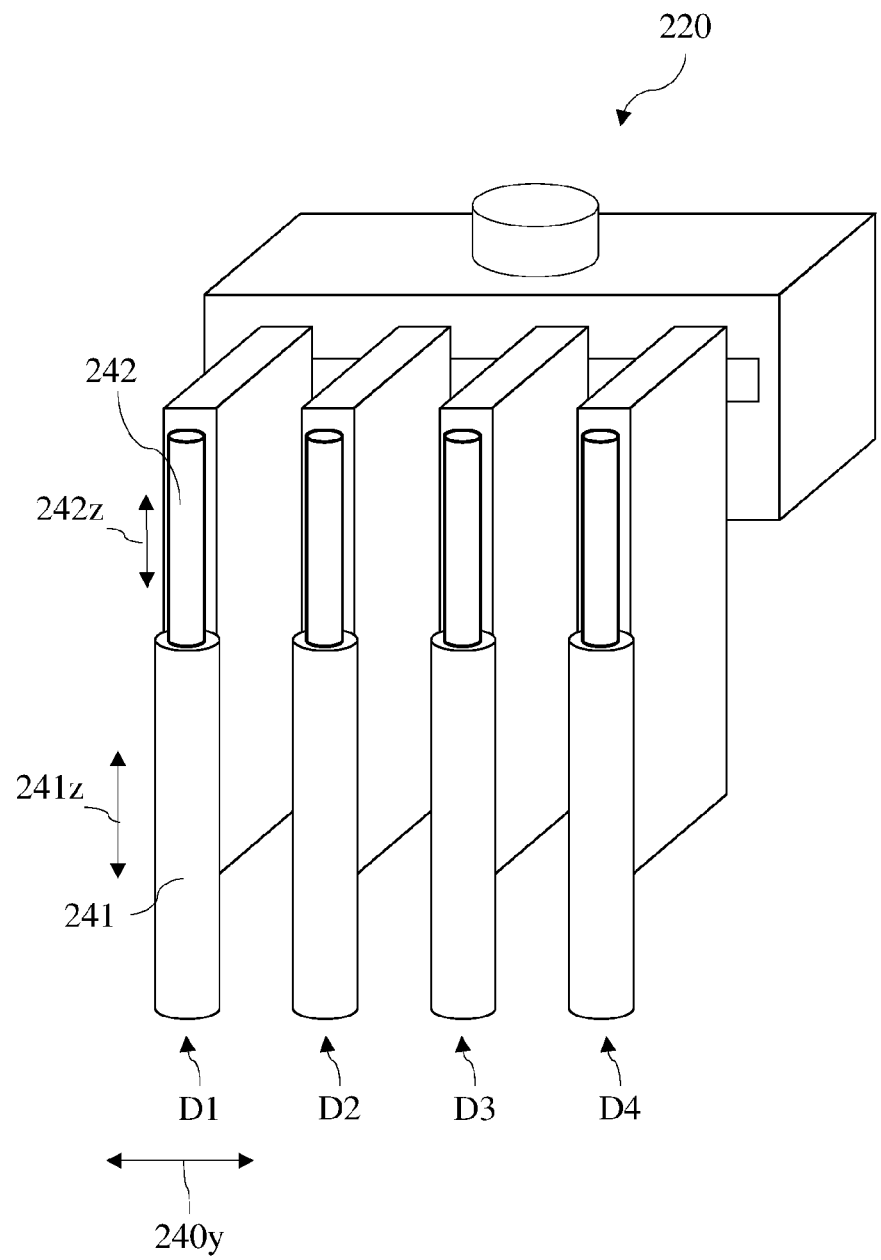
FIG. 39—shows a diagrammatic perspective view of a metering device having four metering channels.

FIG. 39 shows a diagrammatic perspective view of a metering device 220 having four metering channels D1, D2, D3 and D4. Each of those four metering channels D1, D2, D3 and D4 comprises, for example, a tube 241 and a plunger 242, as have been described above. The tube 241 and the plunger 242 are each able to move up and down, as shown by arrows 241z and 242z, respectively, and as explained in detail in connection with FIG. 22. In accordance with arrow 240y, the four metering channels D1, D2, D3 and D4 are displaceable relative to one another horizontally. By means of the four metering channels D1, D2, D3 and D4, printing material or printing materials can be picked up, one after the other or simultaneously, from one or more reservoirs and then, by movement of the metering device 220, transported to one or more target positions defined in all three spatial dimensions, where the printing material or printing materials can be applied to the substrate 60 or to the three-dimensional object P arranged thereon or being constructed thereon.

The invention claimed is:

1. A method for the production and/or treatment of a three-dimensional printed object with a printing material which is dispensed at a target position in the form of discrete three-dimensional printing material elements, wherein a metering device has a metering head and is moved by a transport device to a metering tool provided in a holder; the metering tool is installed in the metering head; the metering device together with the installed metering tool is moved to at least one reservoir in which a supply of printing material is kept; printing material is picked up from that at least one reservoir by means of the metering device; the metering device is moved by the transport device to a target position defined in all three spatial dimensions; and, at that target position, a metered quantity of printing material is applied by means of the metering device to a substrate or to a three-dimensional printed object arranged thereon or being constructed thereon, in order to create one of the printing material elements, the creation of one of the printing material elements being repeated until the three-dimensional printed object has been fully constructed and/or treated.

2. The method according to claim 1, wherein the supply of printing material is a supply of two or more different printing materials and two or more different printing materials are selected and picked up in order to construct and/or treat the three-dimensional printed object with two or more different printing materials.

3. The method according to claim 1, wherein the printing material or printing materials used are liquids, solids dissolved or suspended in liquids, cellular suspensions or biomaterials.

4. The method according to claim 1, wherein the printing material or printing materials used are penetrable or amorphous solids or frozen substances.

5. The method according to claim 1, wherein the printing material or printing materials used are pulverulent or granular solids.

6. The method according to claim 1, wherein by means of the metering device in each case a quantity of printing material is picked up that corresponds quantitatively to one of the printing material elements.

7. The method according to claim 1, wherein the quantity of printing material picked up in each case is weighed gravimetrically before application to the substrate or to the three-dimensional printed object arranged thereon or being constructed thereon; and, based on the result of weighing and preset criteria, a decision is made as to whether the quantity picked up is supplemented or discarded and a new quantity picked up.

8. The method according to claim 1, wherein the metered quantity of printing material applied, in the form of one of the printing material elements, by the metering device in the target position to the substrate or to the three-dimensional printed object arranged thereon or being constructed thereon is hardened and/or fused to the substrate or to the three-dimensional printed object arranged or already partly constructed thereon by application of directed radiation or heat or by some other hardening or polymerising method.

9. The method according to claim 1, wherein the metering tool is discarded and replaced by a fresh metering tool prior to a change of the printing material to be picked up.

10. The method according to claim 1, wherein the metering tool is cleaned prior to a change of the printing material to be picked up.

11. The method according to claim 1, wherein the construction and/or treatment of the three-dimensional printed object is partly effected by means of an additional printing system which is itself likewise configured for the production and/or treatment of a three-dimensional printed object, in which case printing material elements are applied to the substrate or to the three-dimensional printed object arranged thereon or being constructed thereon both by means of the metering device and by means of the additional printing system.

12. The method according to claim 1, wherein the printing material is configured so that the printing material elements applied to the substrate or to the three-dimensional printed object arranged thereon or being constructed thereon has a material-removing action, so that material is removed from the three-dimensional printed object.

13. The method according to claim 12, wherein the material-removing action occurs only after activation of the printing material elements.

14. The method according to claim 12, wherein the printing material is an acid or a solvent.

15. The method according to claim 12, wherein the material-removing action occurs only after activation of the printing material elements by means of heat or radiation.

16. The method according to claim 1, wherein the printing material is configured so that the printing material elements applied to the substrate or to the three-dimensional printed object arranged thereon or being constructed thereon modifies the physical or chemical properties of the three-dimensional printed object point by point.

17. The method according to claim 1, wherein by means of the metering device different printing materials are picked up one after the other from at least two reservoirs and transported to a target position defined in all three spatial dimensions and, at that position, the different printing materials are applied one after the other to the substrate or to the three-dimensional printed object arranged thereon or being constructed thereon.

18. The method according to claim 1, wherein by means of the metering device two or more different printing materials are picked up one after the other from at least two reservoirs, transported to a target position defined in all three spatial dimensions and, at that position, applied to the substrate or to the three-dimensional printed object arranged thereon or being constructed thereon, the two or more different printing materials being mixed with one another in the metering device prior to application.

19. The method according to claim 1, wherein the metering device has at least two metering channels by means of which printing material or two or more different printing materials is/are picked up, one after the other or simultaneously, from one or more of the at least one reservoirs and then transported to at least one target position defined in all three spatial dimensions and, at that position, applied to the substrate or to the three-dimensional printed object arranged thereon or being constructed thereon.

* * * * *